United States Patent [19]

Wang et al.

[11] Patent Number: 5,578,686
[45] Date of Patent: Nov. 26, 1996

[54] PHENOLIC ALLYL ETHERS

[75] Inventors: Pen-Chung Wang, Houston; Donald R. Kelsey, Fulshear, both of Tex.

[73] Assignee: Shell Oil Company, Houston, Tex.

[21] Appl. No.: 505,926

[22] Filed: Jul. 24, 1995

Related U.S. Application Data

[62] Division of Ser. No. 294,272, Aug. 22, 1994, Pat. No. 5,495,051.

[51] Int. Cl.$^6$ .......................... C08L 65/00; C08F 290/00
[52] U.S. Cl. .......................... 525/534; 525/422; 526/262
[58] Field of Search .......................... 526/262; 525/534, 525/422

[56] References Cited

U.S. PATENT DOCUMENTS

| | | |
|---|---|---|
| 4,100,140 | 7/1978 | Zahir et al. . |
| 4,540,829 | 9/1985 | Hefner, Jr. . |
| 5,166,290 | 11/1992 | Hayashi et al. . |
| 5,173,545 | 12/1992 | Hayashi et al. . |
| 5,260,498 | 11/1993 | Ellison . |
| 5,284,929 | 2/1994 | Wang et al. . |

FOREIGN PATENT DOCUMENTS

| | | |
|---|---|---|
| 47-41895 | 10/1972 | Japan . |
| 89/05315 | 11/1988 | WIPO . |

OTHER PUBLICATIONS

"The Development of Tough Bismaleimide Resins," by H. D. Stenzenberger, W. Roemer, & M. Herzog, 1st International SAMPE Symposium, Apr. 7–10, 1986.

"Toughened Bismaleimides: Concepts, Achievements, Directions," by H. D. Stenzenberger, P. König, M. Herzog, W. Römer, 19th International SAMPE Technical Conference, Oct. 13–15, 1987.

"Bismaleimide Resins Improved Novel Toughened Modifiers for BMI Resins," by H. D. Stenzenberger, P. König, M. Herzog, W. Römer, 32nd International SAMPE Symposium, Apr. 6–9, 1987.

*Primary Examiner*—David Buttner

[57] ABSTRACT

A phenolic allyl ether is provided which can be prepared by reacting a polyphenol with an allyl halide, said polyphenol described by the formula

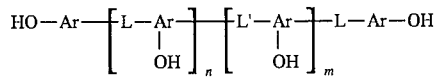

in which Ar is an aromatic moiety, L is a divalent cyclohexanenorbornane linking moiety, L' is a divalent cycloaliphatic moiety, Allyl is a phenolic allyl ether group, and each of m and n is a number within the range of 0 to about 10. Such phenolic allyl ethers include the reaction product of allyl halide with the product of the addition reaction of a phenol and a cyclohexenenorbornene compound such as 5-(3-cyelohexen-1-yl)bicyclo[2.2.1]hept-2-ene. The resulting phenolic allyl ether resins are useful as processing agents for polymaleimides.

6 Claims, No Drawings

PHENOLIC ALLYL ETHERS

This is a division, of application Ser. No. 08/294,272, filed Aug. 22, 1994 now U.S. Pat. No. 5,495,051.

FIELD OF THE INVENTION

This invention relates to novel phenolic allyl ethers and cured products of the phenolic allyl ethers with polymaleimides.

BACKGROUND OF THE INVENTION

Phenolic allyl ether or allyl phenol compounds have been reported as useful as toughing agents for bismaleimides. Bismaleimides are useful in structural and electronic applications where high-performance is required. However, bismaleimides are brittle and require roughing agents. For example, o,o'-diallylbisphenol-A, and diallylbenzenes are reported as toughing agents for bismaleimides.

In addition, polymaleimides have high melting points and they are difficult to process. Therefore it is desirable to have phenolic allyl ethers which can be useful as toughing agents and promote easier processing of polymaleimides.

It is therefore an object of the invention to provide phenolic allyl ethers having low melting points. It is another object of the invention to provide a phenolic allyl ether/polymaleimide composition which is readily processable.

SUMMARY OF THE INVENTION

According to the invention, a phenolic allyl ether is provided which can be described by the formula

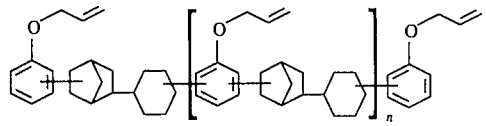

in which n is a number within the range of 0 to about 20.

Further, a phenolic allyl ether is provided which can be described by the formula

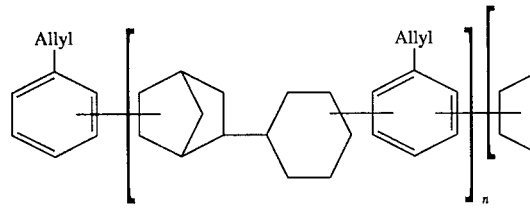

in which Allyl is an allylic ether group and each of m and n is a number within the range of 0 to about 10. The phenolic allyl ether compounds are useful with polymaleimide as the resinous component of electrical laminating and encapsulation formulations.

DETAILED DESCRIPTION OF THE INVENTION

The invention phenolic allyl ether can be prepared by reacting the precursor polyphenols (described below) with an allyl halide such as allyl bromide. The reaction can be carded out at a temperature within the range of from about 80° C., preferably from about 100° C., to about 150° C., preferably to about 130° C. in the presence of a base. The base can be any conventional base such as, for example carbonates and hydroxides of alkali and alkaline earth metals (e.g. sodium carbonate, potassium carbonate, calcium carbonate, sodium hydroxide and potassium hydroxide).

The precursor polyphenols can be described by the formula

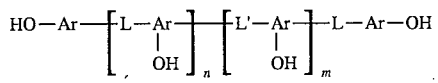

in which Ar is a $C_{6-20}$ aromatic moiety, L is a divalent cyclohexanenorbornane linking moiety, L' is a divalent cycloaliphatic moiety, and each of m and n is a number within the range of 0 to about 10. Such polyphenols can be prepared by the addition reaction of a phenol with a cyclohexenenorbornene compound such as 5-(3-cyclohexen-1-yl) bicyclo[2.2.1]hept-2-ene (herein referred to as the "cyclohexenenorbornene" compound). Suitable phenols include mono- and polynuclear phenols having at least one unsubstituted position ortho- or para- to a phenolic hydroxyl group, such as phenol, cresol, 3,4- and 3,5dimethylphenol, resorcinol, biphenol, 1-naphthol and hisphenol A or F. Phenol is preferred.

Suitable cyclohexenenorbornene compounds include

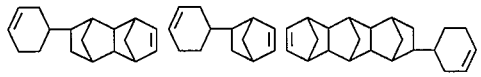

referred to herein as "monoadduct," "diadduct" and "triadduct," respectively, and isomers thereof.

The starting phenol can also include a derivative L' of a cyclo-aliphatic diene such as dicyclopentadiene, cyclopentadiene, norbornadiene dimer, norbornadiene, methylcyclopentadiene dimer, limonene, 1,3- and 1,5-cyclooctadiene, α- and γ-terpinene, 5-vinylnorbornene, 5-(3-propenyl)-2-norborneneand cyclopentadiene oligomers, for example.

The cyclohexenenorbornene compound is an addition product of 4-vinylcyclohexene and cyclopentadiene which can be prepared by contacting 4-vinylcyclohexene and dicyclopentadiene, preferably in the presence of a polymerization inhibitor such as t-butyl catechol, at a temperature of at least about 150° C., preferably about 180° to 260° C., for a time within the range of about 2 hours to about 8 hours. Under these conditions, the dicyclopentadiene is cracked to cyclopentadiene, and the vinylcyclohexene and cyclopentadiene undergo an addition reaction to produce a mixture of mono-, di- and poly-adducts as well as cyclopentadiene oligomers (e.g., trimer, tetraruer, pentamer, etc.). For recovery of one or more desired compounds, the reaction product mixture containing predominately 5-(3-cyclohexen- 1-yl)bicyclo[2.2.1]hept-2-ene is allowed to cool to about 50°–70° C. and is stirred under reduced pressure to strip off unreacted vinylcyclohexene. The reaction product is then purified by fractional vacuum distillation for removal of unwanted by-products including, optionally, di- and polyadducts, and the purified product is passed through an adsorbent bed for removal of t-butyl catechol. Preparation of a vinylcyclohexene/cyclopentadiene adduct is described in U.S. Pat Nos. 5,260,498, and 5,284,929.

The phenolic precursors of the invention phenolic allyl ethers can be prepared by contacting, under addition reaction conditions, one or more of the above-described vinylcyclohexene/cyclopentadiene adduct(s) with a molar excess, preferably about 10 to about 30 moles, of the selected phenol per mole of the adduct(s). The reaction is most efficiently carded out in the presence of a Lewis acid such as $BF_3$, coordination complexes thereof such as boron trifluoride etherate, $AlCl_3$, $FeCl_3$, $SnCl_4$, $ZnCl_2$, silica and silica-alumina complexes and at an elevated temperature within the range of about 70° to about 200° C., preferably about 100° to about 180° C. The reaction is continued until the desired degree of reaction has been completed, usually for a time within the range of about 30 minutes to about 10 hours, preferably about 1 hour to about 3 hours. Preparation of such polyphenols is illustrated in Examples 2 and 4 of U.S. Pat. No. 5,284,929 which is herein incorporated by reference. Reaction of the resulting polyphenols with allyl halides to prepare the invention phenolic allyl ethers is described above and in Example 3 herein.

The invention phenolic allyl ethers can be combined with polymaleimides and cured by exposure to elevated temperature within the range of about 150° to about 250° C. for a time which can vary widely depending on the cure schedule and thickness of the part, generally greater than about 0.25 hour. Suitable polymaleimides for the invention composition include bis- and higher-maleimide resins such as tris- and tetra-maleimide resins.

The preferred polymaleimide resins for the invention composition are N,N'-unsaturated bismaleimides which can be represented by the formula

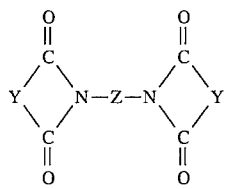

in which Y is a substituted or unsubstituted divalent radical having at least 2 carbon atoms and a carbon-carbon double bond, and Z is a divalent radical containing from about 2 to about 40 carbon atoms. Z can be aliphatic, cycloaliphatic, aromatic or heterocyclic. Z can include heteroatoms and can be substituted or unsubstituted. Examples of bismaleimides which can be employed are N,N'-bismaleimides of ethylene diamine, hexamethylene diamine, trimethylhexamethylene dianline, phenylene dianline, trimethylhexamethylene diamine, methylene dianiline, toluene diamine, 4,4'-diphenylmethane diamine, 3,3'-diphenylsulfone diamine, 4,4'-diphenylether dianline, 4,4'-dicyclohexanemethane diamine, metaxylylene diamine, and 4,4'-diphenylcyclohexane diamine. Various N,N'-bismaleimides are disclosed in U.S. Pat. Nos. 3,562,223, 4,100,140, 4,211,860, 4,211,860 and 4,816,531, for example, and can be prepared by methods known in the art. The N,N'-unsaturated bismaleimides are preferably derived from at least one aromatic diamine. The preferred bismaleimide is bismaleimide of methylenedianiline. The bismaleimide can contain various additives as processing aids. Suitable N,N'-unsaturated bismaleimides are available commercially from Shell Chemical Co. as Compimide® resins, for example.

Other suitable polymaleimide resins include compounds which can be represented by the formula

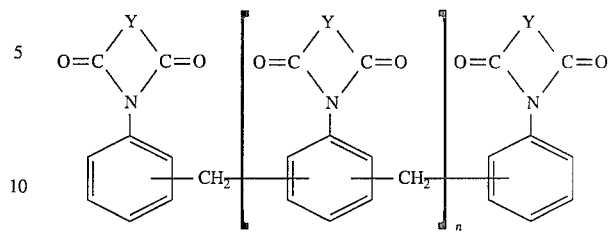

in which Y is a substituted or unsubstituted divalent radical having at least 2 carbon atoms, preferably 2 to 6 carbon atoms, and a carbon-carbon double bond and n is a number having an average value of 0 or greater, preferably an average value from about 0 to about 4. Such polymaleimides are disclosed in U.S. Pat. No. 4,298,720, for example. Specific examples of such compounds include polymethylenephenylenemaleimides having the formula

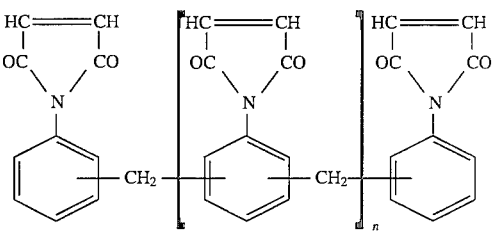

in which n is a number having an average value of 0 or greater, preferably an average value from about 0 to about 4. These polymaleimides can be obtained by reacting an aniline-formaldehyde condensation product with maleic anhydride as described in the above patent.

The amount of the phenolic allyl ether in the blend can vary depending on the process conditions, such as the reactivity of the polymaleimides to the allyl ether groups and reaction temperatures. Generally phenolic allyl ethers will be present in an amount effective to promote ease of processing or to give a tougher cured composition. The phenolic allyl ether is preferably present in a weight ratio of polymaleimides to phenolic allylether within the range from about 10:90 to about 90:10, most preferably from about 40:60 to about 60:40. Optimum properties in the cured resin can be achieved by a staged heating process employing higher temperature in each stage, as illustrated in the Example 3 below.

The invention phenolic allyl ethers are useful, for example, in electrical molding compounds.

ILLUSTRATIVE EMBODIMENT

The following illustrative embodiments describe the novel phenolic allyl ether and the phenolic allyl ether/polymaleimide composition of the invention and are provided for illustrative purposes and are not meant as limiting the invention.

EXAMPLE 1

Preparation of 5-(3-cyclohexen-1-yl)bicyclo[2.2.1]hept-2-ene.

Dicyclopentadiene and 4-vinylcyclohexene in equimolar mixture were heated in an autoclave at 240° C. for 4–4.5 hours. The reaction product was diluted with cyclohexane and passed through a packed bed of alumina to remove the t-butyl-catechol inhibitor introduced with the reactants. The resulting product mixture was distilled in a wiped film evaporator at 3 mm Hg pressure at 90° C. to produce a light fraction containing unreacted vinylcyclohexene and dicyclopentadiene and the mono-adducts of 4-vinylcyclohexene and cyclo-pentadiene. A 150 g sample of this distillate was vacuum distilled using a 10-tray Oldershaw column to give four fractions. The fourth fraction, 65 g, was shown by gas chromatographic analysis to consist of 0.15% dicyclopentadiene, 88.3% endo-5-(3-cyclohexen-1-yl)-2-norbornene, 6.1% exo-5(3-cyclohexen-1-yl)-2-norborneneand two additional components present in the amount of 1.9% and 2.4% which are believed to be isomeric adducts of the formula

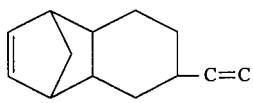

several additional components totalling about 0.4%, 0.4% tricyclopentadiene and about 0.4% unidentified components. Analysis of the fraction by nuclear magnetic resonance indicated about 87 mole percent of the endo adduct, about 9 mole percent of the exo adduct and about 5% of the isomeric adducts.

EXAMPLE 2

Preparation of Monoadduct Polyphenol.

To a reactor equipped with a stirrer, condensor and additional funnel were added 188.2 g (2.0 mole) of phenol and 1.0 g of $BF_3 \cdot Et_2O$. The mixture was heated to 70° C. and 13.67 g of 5-(3-cyclohexen-1-yl)bicyclo[2.2.1]hept-2-ene was added over a 20-minute period. The temperature was raised to 150° C. over a 1½-hour period and was held for about 2½ hours. Unreacted phenol was distilled off. The recovered polyphenol had a terminal hydroxyl group concentration of 0.495 equivalent/100 g and a melting point of 70°–80° C.

EXAMPLE 3

Preparation and Curing of Allyl Ether A.

Allyl bromide (32.66 g) in 50 ml of toluene was added over 60 minutes to the reaction mixture. Then the reaction temperature was raised to 125° C. and held there for 12 hours. After cooling, the reaction mixture was filtered and filtrates were concentrated to give a liquid composition (Recovered 57.1 g). Confirmation of the above structural formula for the product where n is 0.5 is made by nuclear magnetic resonance spectra. The preferred range of n is a number within the range of 0 to about 20, more preferably 0 to about 3 for use with the polymaleimides.

1.39 g of Resin A was cured with 1.36 g of bismaleimide of methylene dianiline ("MDA"; melting point 150° C.) at 200° C. for 4 hours and 240° C. for 2 hours to give a cured material having Tg>300° C. and 10% wt. loss temp in Thermal Gravimetric Analysis (Air) at 450° C.

We claim:

1. A composition comprising the phenolic allyl ether having the formula

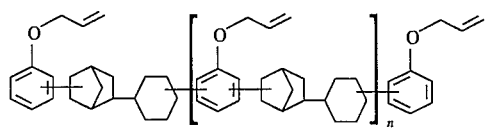

in which n is a number within the range of 0 to about 20 and a polymaleimide.

2. A cured product of claim 1.

3. The composition of claim 1 wherein the polymaleimide is the bismaleimide of methylene dianiline.

4. A cured product of claim 3.

5. A composition comprising the phenolic allyl ether having the formula

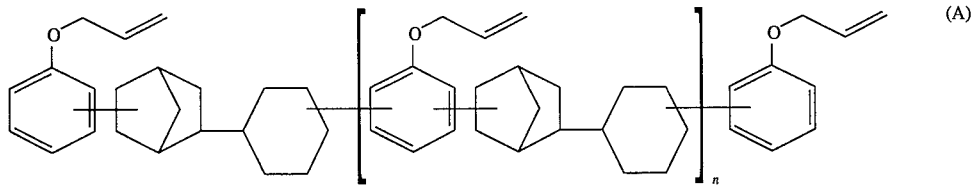

(A)

A mixture of 50 g of a polyphenol which has been prepared from phenol and 5-(3-cyclohexen-1-yl)bicyclo[2,2,1]hept-2-ene according to the procedure in Example 2 above (a terminal hydroxyl group concentration of 0.495 equivalent//100 g and a melting point of 70°–80° C.), 18.66 g of potassium carbonate and 200 ml of toluene was placed in a 1 liter round bottomed flask equipped with a mechanical stirrer and a condenser, and warmed to 120°–130° C. while stirring. Water was removed by azeotropic distillation until completion, then the temperature was lowered to 80–90° C.

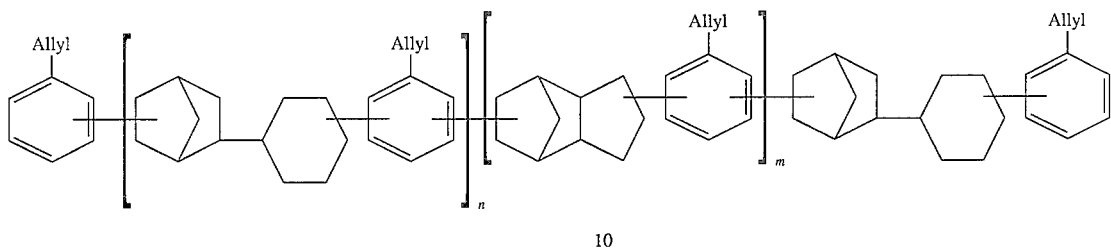
in which Allyl is an allylic ether group and each of m and n is a number within the range of 0 to about 10 and a polymaleimide.
6. A cured product of claim 5.